(12) United States Patent
Berg et al.

(10) Patent No.: US 6,371,982 B2
(45) Date of Patent: *Apr. 16, 2002

(54) GRAFT STRUCTURES WITH COMPLIANCE GRADIENTS

(75) Inventors: Todd Allen Berg, Lino Lakes; David S. Goldsteen, Minneapolis, both of MN (US)

(73) Assignee: St. Jude Medical Cardiovascular Group, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/946,741

(22) Filed: Oct. 9, 1997

(51) Int. Cl.$^7$ .................................................. A61F 2/06
(52) U.S. Cl. ........................................ 623/1.4; 623/1.13
(58) Field of Search ............................ 623/1, 12, 1.13, 623/139, 1.4; 606/194

(56) References Cited

U.S. PATENT DOCUMENTS

| | | | |
|---|---|---|---|
| 4,214,587 A | 7/1980 | Sakura, Jr. .................... 128/334 |
| 4,459,252 A | 7/1984 | MacGregor ................. 264/46.9 |
| 4,487,567 A | 12/1984 | Possis et al. ................. 425/403 |
| 4,503,569 A | 3/1985 | Dotter ............................ 3/1.4 |
| 4,546,499 A | 10/1985 | Possis et al. .................... 623/1 |
| 4,562,597 A | 1/1986 | Possis et al. .................... 623/1 |
| 4,592,754 A | 6/1986 | Gupte et al. .................... 623/1 |
| 4,601,718 A | 7/1986 | Possis et al. .................... 623/1 |
| 4,605,406 A | 8/1986 | Cahalan et al. ................. 623/1 |
| 4,617,932 A | 10/1986 | Kornberg ..................... 123/334 |
| 4,629,458 A | 12/1986 | Pinchuk .......................... 623/1 |
| 4,632,842 A | 12/1986 | Karwoski et al. ............... 427/2 |
| 4,657,544 A | 4/1987 | Pinchuk .......................... 623/1 |
| 4,665,906 A | 5/1987 | Jervis ........................... 128/92 |

(List continued on next page.)

FOREIGN PATENT DOCUMENTS

| | | | |
|---|---|---|---|
| AU | 670239 | 7/1996 | ............ A61F/2/06 |
| EP | 0 539 237 A1 | 4/1993 | ............ A61F/2/06 |
| EP | 0 637 454 A1 | 2/1995 | .......... A61M/25/10 |
| EP | 0 680 734 A2 | 11/1995 | ............ A61F/2/06 |
| EP | 0 684 022 A2 | 11/1995 | ............ A61F/2/06 |
| WO | WO 94/06372 | 3/1994 | ............ A61F/2/04 |
| WO | WO 96/01591 | 1/1996 | ........... A61B/17/22 |
| WO | WO 96/01599 | 1/1996 | ............ A61F/2/06 |
| WO | WO 96/18361 | 6/1996 | ............ A61F/2/06 |

*Primary Examiner*—Bruce Snow
(74) *Attorney, Agent, or Firm*—Fish & Neave; Robert R. Jackson; Richard M. Feustel, Jr.

(57) ABSTRACT

A distensible artificial tubular graft structure is provided that has a compliance gradient. The graft may be used to repair a patient's body organ tubing. For example, the graft may be used to replace or supplement portions of a patient's vascular system. The ends of the graft structure may have compliances that are matched to the compliances of the body organ tubing to which they are attached. Distensible compliance-matched connector structures may be used to attach the graft to the body organ tubing.

2 Claims, 5 Drawing Sheets

U.S. PATENT DOCUMENTS

| | | | |
|---|---|---|---|
| 4,705,517 A | 11/1987 | DiPisa, Jr. | 623/12 |
| 4,718,907 A | 1/1988 | Karwoski et al. | 623/12 |
| 4,733,665 A | 3/1988 | Palmaz | 128/343 |
| 4,738,740 A | 4/1988 | Pinchuk et al. | 156/167 |
| 4,743,252 A | 5/1988 | Martin, Jr. et al. | 623/1 |
| 4,759,757 A | 7/1988 | Pinchuk | 623/1 |
| 4,787,899 A | 11/1988 | Lazarus | 623/1 |
| 4,798,606 A | 1/1989 | Pinchuk | 623/1 |
| 4,892,539 A | 1/1990 | Koch | 623/1 |
| 4,909,979 A | 3/1990 | Possis et al. | 264/571 |
| 4,955,899 A | 9/1990 | Della Corna et al. | 623/901 |
| 5,037,377 A | 8/1991 | Alonso | 600/36 |
| 5,061,275 A | 10/1991 | Wallsten et al. | 623/1 |
| 5,084,065 A | 1/1992 | Weldon et al. | 623/1 |
| 5,100,422 A | 3/1992 | Berguer et al. | 606/151 |
| 5,104,399 A | 4/1992 | Lazarus | 623/1 |
| 5,104,400 A | 4/1992 | Berguer et al. | 264/132 |
| 5,116,360 A | 5/1992 | Pinchuk et al. | 623/1 |
| 5,122,154 A | 6/1992 | Rhodes | 606/198 |
| 5,135,467 A | 8/1992 | Citron | 600/16 |
| 5,152,782 A | 10/1992 | Kowligi et al. | 623/1 |
| 5,163,951 A | 11/1992 | Pinchuk et al. | 623/158 |
| 5,211,658 A | 5/1993 | Clouse | 623/1 |
| 5,211,683 A | 5/1993 | Maginot | 128/898 |
| 5,246,451 A | 9/1993 | Trescony et al. | 623/1 |
| 5,246,452 A | 9/1993 | Sinnott | 623/1 |
| 5,275,622 A | 1/1994 | Lazarus et al. | 623/1 |
| 5,282,847 A | 2/1994 | Trescony et al. | 623/1 |
| 5,304,220 A | 4/1994 | Maginot | 623/1 |
| 5,306,240 A | 4/1994 | Berry | 604/51 |
| 5,316,023 A | 5/1994 | Palmaz et al. | 128/898 |
| 5,360,443 A | 11/1994 | Barone et al. | 623/1 |
| 5,366,504 A | 11/1994 | Andersen et al. | 623/11 |
| 5,387,235 A | 2/1995 | Chuter | 623/1 |
| 5,395,349 A | 3/1995 | Quiachon et al. | 604/248 |
| 5,397,345 A | 3/1995 | Lazarus | 623/1 |
| 5,413,598 A | 5/1995 | Moreland | 623/1 |
| 5,425,765 A | 6/1995 | Tiefenbrun et al. | 623/12 |
| 5,429,144 A | 7/1995 | Wilk | 128/898 |
| 5,443,497 A | 8/1995 | Venbrux | 623/1 |
| 5,443,499 A | 8/1995 | Schmidt | 623/1 |
| 5,456,712 A | 10/1995 | Maginot | 623/1 |
| 5,489,295 A | 2/1996 | Piplani et al. | 623/1 |
| 5,496,364 A | 3/1996 | Schmitt | 623/1 |
| 5,496,365 A | 3/1996 | Sgro | 623/1 |
| 5,507,769 A | 4/1996 | Marin et al. | 606/198 |
| 5,509,931 A | 4/1996 | Schmidt | 623/1 |
| 5,522,880 A | 6/1996 | Barone et al. | 623/1 |
| 5,562,725 A | 10/1996 | Schmitt et al. | 623/1 |
| 5,584,875 A | 12/1996 | Duhamel et al. | 623/1 |
| 5,584,876 A | 12/1996 | Bruchman et al. | 623/1 |
| 5,607,463 A | 3/1997 | Schwartz et al. | 623/1 |
| 5,607,464 A | 3/1997 | Trescony et al. | 623/1 |
| 5,609,624 A | 3/1997 | Kalis | 623/1 |
| 5,628,782 A | 5/1997 | Myers et al. | 623/1 |
| 5,628,786 A | 5/1997 | Banas et al. | 623/1 |
| 5,628,788 A | 5/1997 | Pinchuk | 623/1 |
| 5,632,772 A | 5/1997 | Alcime et al. | 623/1 |
| 5,653,747 A | 8/1997 | Dereume | 623/1 |
| 5,922,019 A * | 7/1999 | Hankh et al. | 623/1 |
| 5,938,697 A * | 8/1999 | Killion et al. | 623/1 |

* cited by examiner

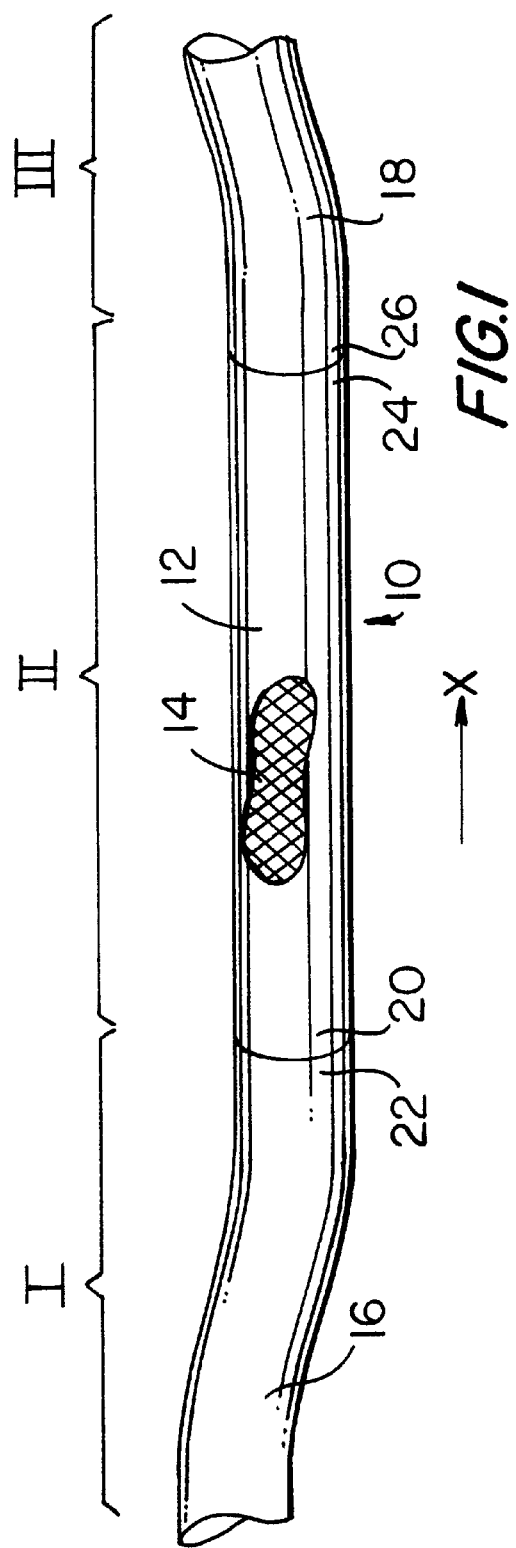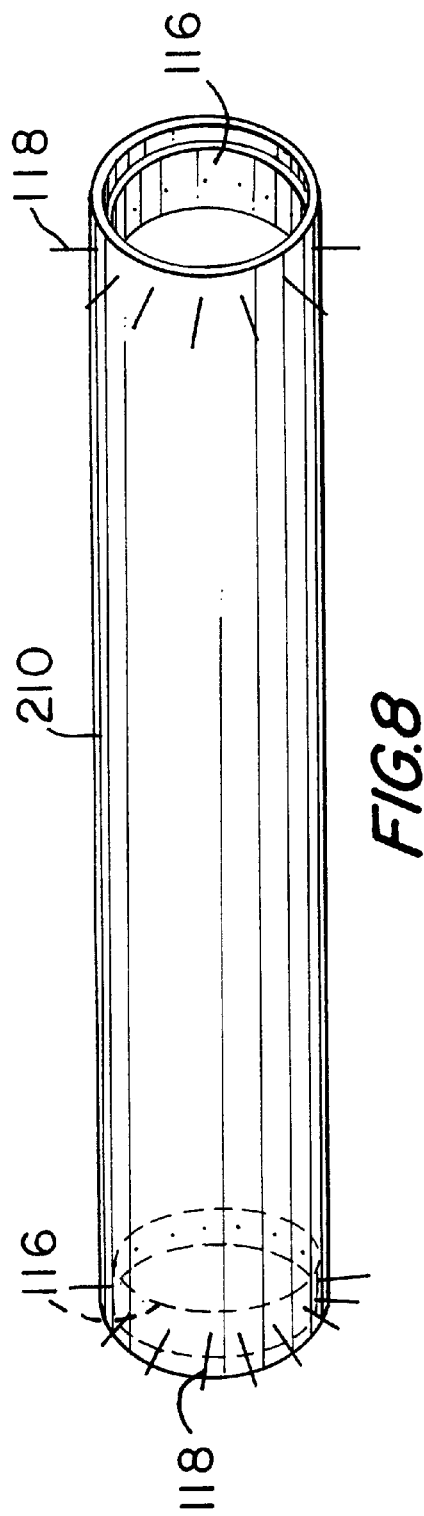

GRAFT STRUCTURES WITH COMPLIANCE GRADIENTS

BACKGROUND OF THE INVENTION

This invention relates to tubular graft structures for replacing or supplementing a patient's natural body organ tubing. More particularly, the invention relates to tubular graft structures in which the elastic compliance of the graft varies along the length of the graft.

A patient's weakened or diseased body organ tubing can often be repaired by replacing or supplementing the patient's existing natural body organ tubing with an artificial graft structure. One of the goals in using artificial grafts to repair natural body organ tubing is to match the characteristics of the artificial graft to those of the natural graft as closely as possible. For example, an important property of artificial grafts used to repair blood vessels is that they be distensible like natural blood vessels. Distensible grafts are less susceptible to blood clot formation than other grafts, because distensible grafts pulsate during blood flow, which tends to hinder blood clot formation. As described in Goldsteen et al. U.S. patent application Ser. No. 08/839,080, filed Apr. 23, 1997, distensible grafts may be formed from a nitinol mesh frame covered with a silicone coating.

The natural distensibility of an artery allows energy to be stored in the walls of the artery during periods of systolic blood pressure and allows energy to be released from the walls during periods of diastolic blood pressure. Storage and subsequent release of energy by the distensible artery walls helps to sustain blood flow.

The distensibility of a given portion of natural body organ tubing or artificial graft tubing can be quantified by its compliance, which is defined as the elastic change in diameter of the tubing per unit fluid pressure inside the tubing. The compliance of an artery is determined by the amount of elastin fibers in the artery wall. The downstream or distal portions of the artery are typically less compliant than the upstream or proximal portions of the artery.

This gradient in the compliance of the artery allows the upstream portions of the artery to match the relatively high compliance of vessels in the upstream artery environment and allows the downstream portions of the artery to match the lower compliance of the peripheral blood vessel beds fed by the downstream portions of the artery. Because the compliance of each portion of the artery is matched to the compliance of the blood vessels connected to that portion of the artery, stress and possible damage to the artery walls due to abrupt transitions in compliance is reduced.

It is therefore an object of the present invention to provide a distensible artificial graft having compliance properties similar to the compliance properties of the natural body organ tubing of a patient.

It is also an object of the present invention to provide a distensible artificial graft that has a compliance gradient and is compliance matched to the body organ tubing of a patient.

SUMMARY OF THE INVENTION

These and other objects of the invention are accomplished in accordance with the principles of the present invention by providing a distensible artificial graft that may be used to replace or; supplement diseased or damaged natural body organ tubing. For example, the graft may be used to repair blocked blood vessels. Because the graft is distensible, in vascular applications the graft pulsates like natural blood vessels, which may reduce the incidence of blood clot formation.

The graft has a compliance (i.e., change in diameter of the graft per unit pressure inside the graft) that varies along the length of the graft. This compliance gradient allows the graft to create a smooth transition between portions of body organ tubing with different compliances. For example, the graft may be used to connect an upstream portion of an artery (which has a relatively high compliance) with a downstream portion of the artery (which has a relatively low compliance). By matching the magnitude of the compliance at each end of the graft with the portion of body organ tubing to which it is connected, abrupt transitions in compliance are avoided. Avoiding such abrupt transitions reduces stress and possible damage to the body organ tubing in the vicinity of the graft.

The graft may be formed from any suitable distensible tubular structure in which compliance can be varied along the length of the structure. For example, the graft may be formed from a flexible tubular mesh frame covered with an elastic coating. A suitable mesh may be formed from nitinol wire. A suitable coating is silicone.

The compliance gradient may be formed by varying the density of the mesh along the length of the graft. Higher density mesh is generally less compliant than lower density mesh. Mesh density can be controlled during graft fabrication by varying the pattern of the mesh. For example, a tighter weave or braid increases the density of the mesh. Preferably, the density of the mesh is controlled by varying the pic count of the mesh. Other techniques that may be used to control the density of the mesh include varying the size of the nitinol wire and varying the number of wire strands that are used to form the mesh.

If desired, the compliance gradient may be formed by varying the thickness of the elastic coating used to cover the frame. Portions of the graft where the coating is thick are less compliant than portions of the graft where the coating is thin. If the graft is formed primarily from a single material (e.g., a polymeric substance), the graft compliance can be controlled by varying the thickness of the material.

A compliance gradient may be created by compressing a conical frame into a cylindrical graft shape. The conical frame may be formed on a conical mandrel. If a heat sensitive memory-effect metal such as nitinol is used as the frame material, the frame may initially be formed in a cylindrical shape and subsequently stretched and heat-set in the desired conical shape. After the conical frame shape is created, the frame is radially compressed into a cylindrical shape and covered with a suitable coating such as silicone. The portions of the frame that were the largest radially before compression contribute a radial outward bias to the completed graft structure. The outward bias of such frame portions increase the compliance of the corresponding portions of the graft.

Another way in which to create the compliance gradient for the graft is to vary the properties of the materials used to form the graft. For example, coatings of different durometer or Young's modulus may be used to cover different portions of a frame structure. If desired, the porosity of the graft may be varied to create the compliance gradient.

Distensible connector structures may be used to attach the graft to the body organ tubing. One suitable distensible connector structure is an elastic ring with radially extending barbs or hooks. When the graft is installed in the patient, the elastic ring expands to force the barbs through the graft and into the body organ tubing, thereby attaching the graft to the body organ tubing. If desired, the compliance of such connector structures can be matched to the compliance of the body organ tubing at the attachment site.

Further features of the invention, its nature and various advantages will be more apparent from the accompanying drawings and the following detailed description of the preferred embodiments.

BRIEF DESCRIPTION OF THE DRAWINGS

FIG. 1 is a partially cut-away perspective view of body organ tubing in which a section of tubing has been replaced by a graft in accordance with the present invention.

FIG. 6b is a graph showing the relationship between pore size and compliance (length) for the graft of FIG. 6a.

FIG. 7b is a graph showing the relationship between pore quantity and compliance (length) for the graft of FIG. 7a.

FIG. 8 is a perspective view of a graft structure showing illustrative distensible graft connector structures in accordance with the present invention that are used to connect the graft to natural body organ tubing.

DETAILED DESCRIPTION OF THE PREFERRED EMBODIMENTS

Figure 2:
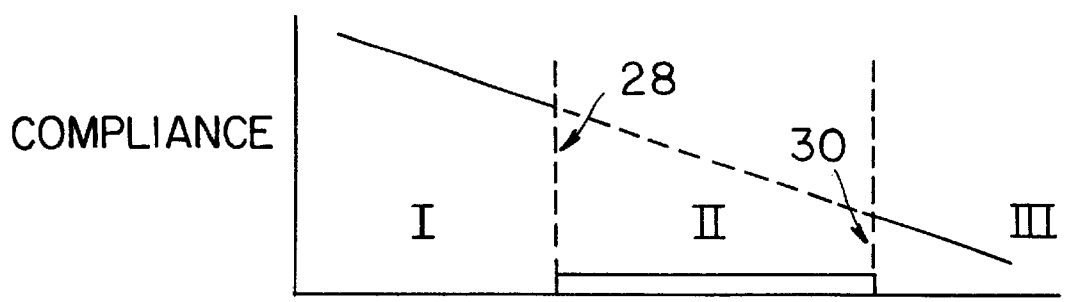
FIG. 2 is a graph of compliance plotted versus distance along the longitudinal axis of a prior art graft structure.

An illustrative distensible artificial graft in accordance with the present invention is shown in FIG. 1. Graft 10 may be a structure formed from a flexible coating 12 covering a frame 14. The preferred materials for forming frame 14 of graft 10 are metals, although polymeric materials may also be used. The presently most preferred material is a braid of nitinol wire. Coating 12 is preferably an elastic biocompatible material such as silicone, which fills the apertures formed by the wires in frame 14. Other materials that may be used for coating 12 include polymeric materials such as stretchable urethane, stretchable polytetrafluoroethylene (PTFE), natural rubber, and the like.

If desired, coating 12 can be formed with microscopic pores to help improve bio-compatibility. A preferred method of providing a desired porosity is to make coating 12 from an elastic material that is mixed with particles of a material that can be removed (e.g., by vaporization) after coating 12 has been applied to frame 14. When the particles are removed, voids are left in coating 12 that give it porosity. The degree of porosity of coating 12 influences its elasticity, so the compliance of coating 12 may be controlled by varying the porosity of coating 12.

If desired, graft 10 may be provided with additional coatings such as medicated coatings, hydrophilic coatings, smoothing coatings, collagen coatings, human cell seeding coatings, etc., as described in the above-mentioned Goldsteen et al. U.S. patent application Ser. No. 08/745,618, filed Nov. 7, 1996, which is hereby incorporated by reference herein in its entirety. The above-described preferred porosity of coating 12 helps graft 10 to retain these coatings.

In the illustrative example of FIG. 1, graft 10 has been used to replace a section of body organ tubing between body organ tubing 16 and body organ tubing 18. Body organ tubing 16 and 18 appears elongated in FIG. 1, but graft 10 may also be used to connect body organ tubing of any suitable shape. As defined herein, the term "body organ tubing" generally refers to elongated fluid-containing body organ tissues such as blood vessels and the like and to similar but less elongated body organ tissue structures such as portions of the heart wall. Body organ tubing may be vascular tubing or any other type of body organ tubing.

In accordance with the present invention, the compliance of distensible graft 10 at end 20 is matched to the compliance of body organ tubing 16 at end 22. In addition, the compliance of graft 10 at end 24 is matched to the compliance of body organ tubing 18 at end 26. Repairs of the type shown in FIG. 1 can be made to any desired type of body organ tubing, but compliance matching is particularly important in blood vessel repairs to reduce stress due to abrupt transitions in compliance between ends 20 and 22 and between 24 and 26.

In conventional graft arrangements, the compliances of body organ tubing and grafts are not matched. As shown in FIG. 2, the compliance of the graft of region II does not match the compliance of the body organ tubes of regions I and III at transitions 28 and 30. In part, the abruptness of transitions 28 and 30 is due to the relatively low compliance of the conventional graft of region II. The abruptness of transitions 28 and 30 is also exacerbated by the mismatch between the gradients of the body organ tubing compliances of regions I and III and the lack of any gradient in the compliance of the graft in region II.

With the arrangement of the present invention, the magnitude and the gradient of the compliance of graft 10 (FIG. 1) may be matched to the magnitude and gradient of the compliance of the body organ tubing section that was replaced by graft 10, as shown by graft compliance curve 32. The graft compliance at end 38 of curve 32 is matched with the body organ tubing compliance at end 40 of curve 34 and the graft compliance at end 42 of curve 32 is matched with the body organ tubing compliance at end 44 of curve 36. Matching the compliance gradient and the compliances of the ends of graft 10 with the compliances of the respective ends of the body organ tubing reduces stress and possible damage to the body organ tubing that might otherwise result using a conventional arrangement such as shown in FIG. 2.

It is not necessary for the match between the compliance gradient and compliance at the ends of graft 10 and the ends of the body organ tubing to be perfect. For example, a suitable graft 10 might have the compliance shown by graft compliance curve 46. Although the match of the graft of curve 46 is not as good as the graft of curve 32, the graft of compliance curve 46 is significantly better at reducing stress and possible body organ tubing damage due to abrupt transitions than the conventional graft of FIG. 2.

Grafts having compliances such as those shown by curves 32 and 46 are suitable for repairing sections of body organ tubing having the compliances of curves 34 and 36. Moreover, the smooth monotonic gradient of the compliances of curves 32 and 46 avoids abrupt transitions in compliance within graft 10 (FIG. 1) and optimizes the hemodynamics of graft 10.

Figure 3A:
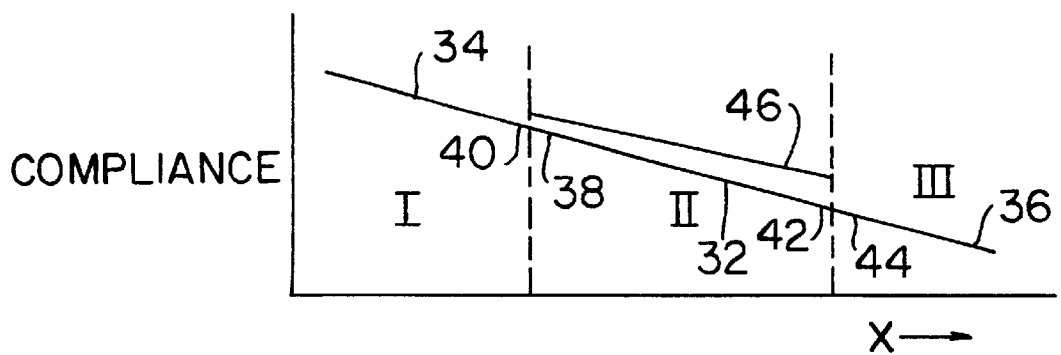
FIGS. 3a and 3b are and graphs of compliance plotted versus distance along the longitudinal axis of graft structures in accordance with the present invention.
Figure 3B:
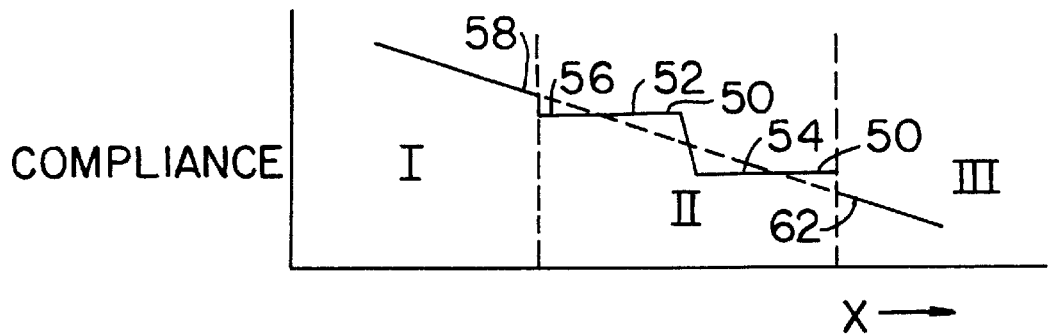

If desired, grafts may be formed that have less smooth compliance gradients than those shown in FIG. 3a. For example, the magnitude and the gradient of the compliance of graft 10 of FIG. 1 may be as shown in FIG. 3b. In compliance curve 50 of FIG. 3b, the magnitude of the graft compliance in portion 52 is at a first level and the graft compliance in portion 54 is at a second level. Nevertheless, the graft compliance at end 56 matches the body organ compliance at end 58 and the graft compliance at end 60 matches the body organ tubing compliance at end 62. Matching the compliances of the ends of the graft of curve 50 with the compliances of the respective ends of the body organ tubing reduces stress and possible damage to the body organ tubing in the vicinity of the transitions between the body organ tubing and graft. Although there is a transition in the compliance level in the center of the graft of curve 50, a transition in that location is generally less likely to cause tissue damage than a comparable transition at a connection (anastomosis) between the graft and body organ tubing.

The compliance profiles of FIGS. 3a and 3b are illustrative only. Other compliance profiles may be used if desired. In general, the compliance of an off-the-shelf graft will not be perfectly matched to the compliance of a given section of body organ tubing to be repaired. However, the grafts of the present invention preferably have compliance gradients and compliance magnitudes at their ends that match the body organ tubing to which they are connected well enough to reduce the stress and potential body organ tubing damage that may result using conventional grafts.

Figure 4A:
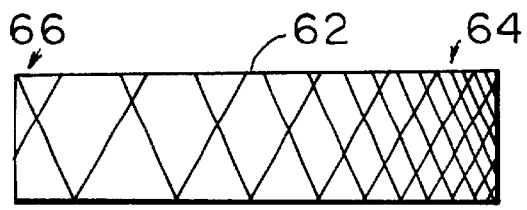
FIGS. 4a–d are side views of various graft structures in accordance with the present invention in which the compliance of the graft varies as a function of distance along the longitudinal axis of the graft.

Various techniques may be used to form graft structures with compliance gradients in accordance with the present invention. A number of illustrative structures are shown in FIGS. 4a–d. As shown in FIG. 4a, a graft with a compliance gradient may be formed by varying the density of the metal mesh used to form frame 62. The density of frame 62 varies as a function of the distance along the longitudinal axis of frame 62. The density of frame 62 is higher at end 64 than at end 66, so the compliance of the graft formed using frame 62 is greater at end 66 (where it is relatively easier to radially expand the graft) than at end 64 (where it is relatively more difficult to radially expand the graft). If frame 62 is a formed from metal wire, the density (and therefore the compliance) of frame 62 is preferably varied by changing the pic count (the number of wire intersections per inch along a single longitudinally oriented line on the surface of frame 62) along the length of frame 62. The density and compliance of frame 62 may also be varied by changing the strand count (e.g., 16, 32, or 64, etc. or by changing the diameter of the wire in the frame. Compliance may also be varied by changing the pattern of weave or braid that is used to form the mesh frame. Tightly woven or braided patterns generally have lower compliances than loosely woven or braided patterns. After being formed with a compliance gradient, frame 62 may be covered with a coating such as coating 12 of FIG. 1.

If desired, the compliance gradient may be formed by varying the thickness of elastic coating 12.

Figure 4B:
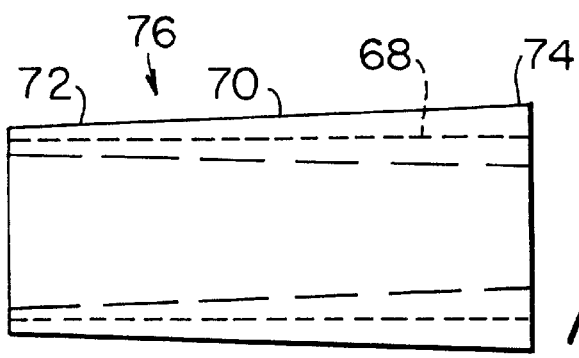

As shown in FIG. 4b, frame 68 is covered with coating 70, which is relatively thinner at end 72 and relatively thicker at end 74. As a result, the compliance of graft 76 is greater at end 72 (where the thin coating makes it relatively easier to radially expand the graft) than at end 74 (where the thick coating makes it relatively difficult to radially expand the graft).

Figure 4C:
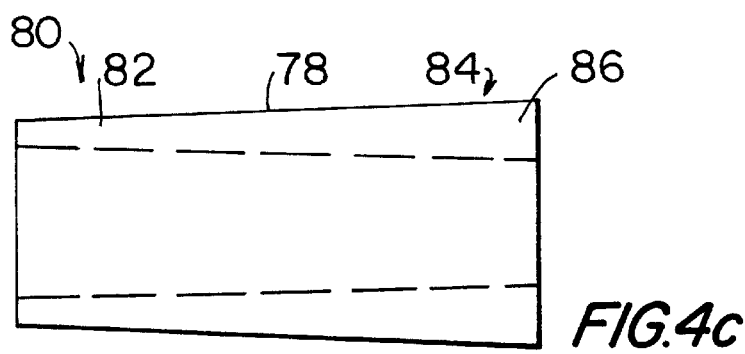

If the graft is formed from a flexible polymer or other suitable elastic material without an internal frame, the thickness of the polymer can be varied as a function of the distance along the longitudinal axis of the graft. As shown in FIG. 4c, such a graft 78 has a compliance gradient, because the compliance at end 80 (where thin graft wall 82 makes it relatively easier to radially expand the graft) is more than the compliance at end 84 (where thick graft wall 86 makes it relatively difficult to radially expand the graft).

Figure 4D:
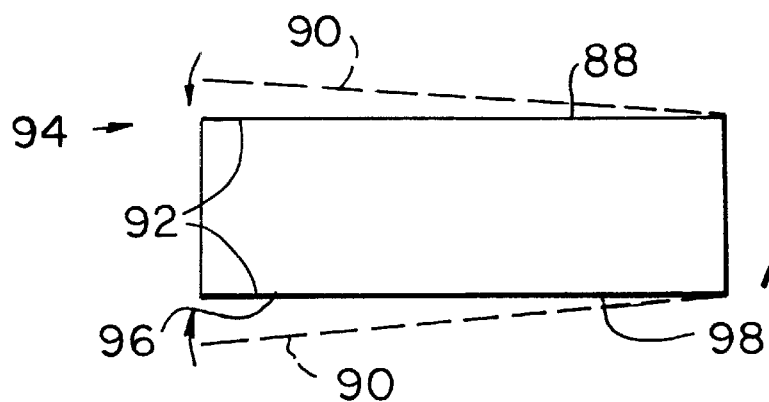

Another technique for creating a graft with a compliance gradient involves using a frame formed from a heat sensitive metal such as nitinol. As shown in FIG. 4d, nitinol frame 88 is initially formed in conical shape 90 by directly weaving or braiding frame 88 into that shape or by stretching a cylindrical mesh into conical shape 90 and setting shape 90 with a heat treatment. The conically-heat-set frame in shape 90 is then forced to assume shape 92 (e.g., by radially compressing frame 88 within a cylindrical tube). A coating such as coating 12 is applied to frame 88 while frame 88 has shape 92, thereby forming graft 94. At end 96, the compressed frame 88 desires to expand radially outward to regain uncompressed shape 90, so end 96 is prestressed for radial expansion. At end 98, frame 88 is already nearly in uncompressed shape 90, so there is relatively little radial expansion prestressing. Graft 94 therefore has a compliance gradient, because the compliance of graft 94 is higher near end 96 than near end 98.

The compliance gradients of the grafts of FIGS. 4a–d are relatively smooth and continuous, such as shown by graft compliance curves 32 and 46 of FIG. 3a. Smooth gradients are desirable because they optimize the hemodynamics of the graft. If other techniques are used to form the graft, compliance gradients such as the two-level stepped compliance gradient of FIG. 3b can be obtained. Although the hemodynamics of a graft with a stepped compliance gradient may not be as optimum as the hemodynamics provided by a graft with a smooth compliance gradient, the performance of such grafts may be satisfactory. Grafts with stepped compliance gradients may also be easier to fabricate in some cases than grafts with smooth compliance gradients.

Figure 5A:
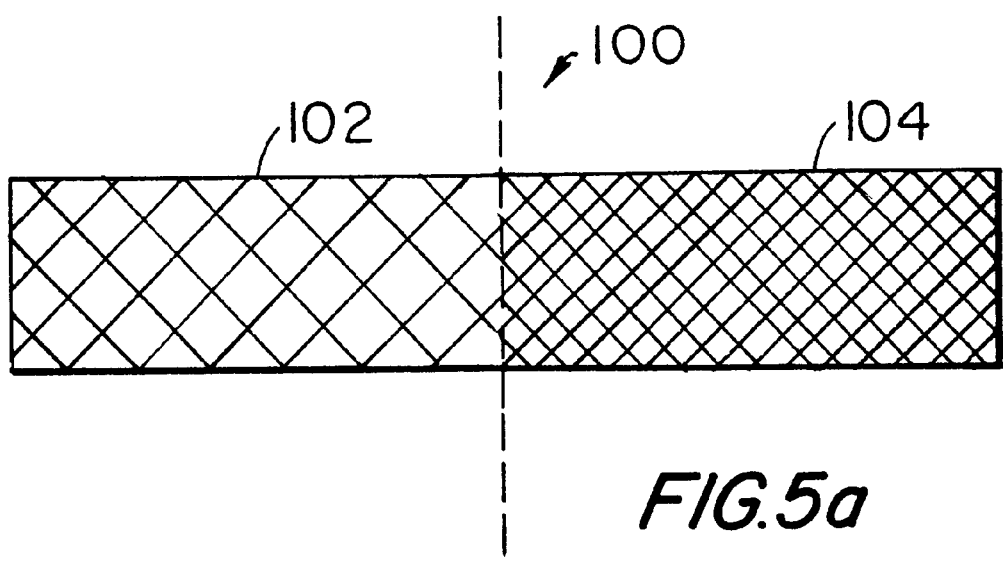
FIGS. 5a and 5b are side views of additional graft structures in accordance with the present invention in which the compliance of the graft varies as a function of distance along the longitudinal axis of the graft.

Grafts with stepped compliance gradients may be formed using a variety of techniques. As shown in FIG. 5a, graft frame 100 may be formed with different densities. Frame portion 102 may have a lower density (and therefore higher compliance) than frame portion 104. If frame 100 is a formed from metal wire, the compliance of frame 100 is preferably varied by changing the pic count (the number of wire intersections per inch along a single longitudinally oriented line on the surface of frame 100) used for portions 102 and 104. Portions 102 and 104 may also be formed with different compliances by changing the pattern of weave or braid that is used to form the mesh frame, or changing the diameter of the wire in the frame. After forming frame 100 with the two-step compliance pattern shown in FIG. 5a, frame 100 may be covered with a coating such as coating 12 of FIG. 1 to complete the graft.

If desired, a stepped compliance pattern may be formed by stretching or compressing the frame and heat-setting the frame, as described in connection with FIG. 4d.

Figure 5B:
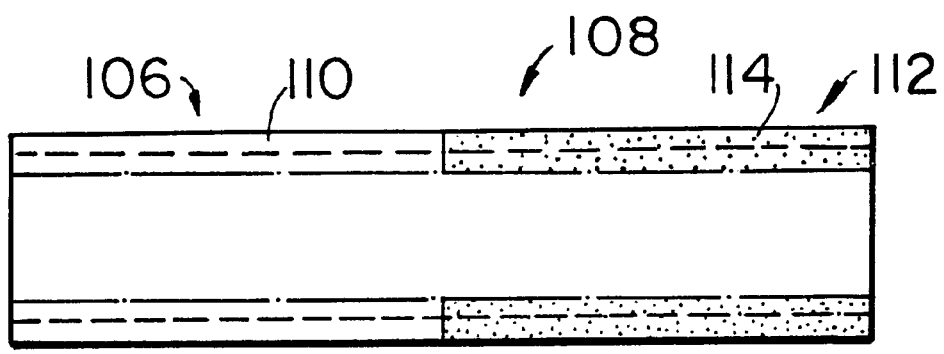

Another technique for forming a graft with a stepped compliance pattern involves varying the compliance of the graft by varying the properties of the graft coating. As shown in FIG. 5b, end 106 of frame 108 is covered with coating 110 and end 112 of frame 108 is covered with coating 114. The compliance of ends 106 and 112 will generally differ depending on the respective material properties (e.g., durometer, Young's modulus, etc.) of coatings 110 and 112. If desired, multiple layers of coatings may be provided to vary the compliance of the graft. Smooth graft compliance profiles (such as shown by curves 32 and 46 of FIG. 3a) may be obtained by smoothly varying the properties and the number of layers of graft coating that are used.

If desired, the compliance of the graft may be varied by controlling the size and/or quantity of pores in the graft. This is illustrated in FIGS. 6 and 7.

Figure 6A:
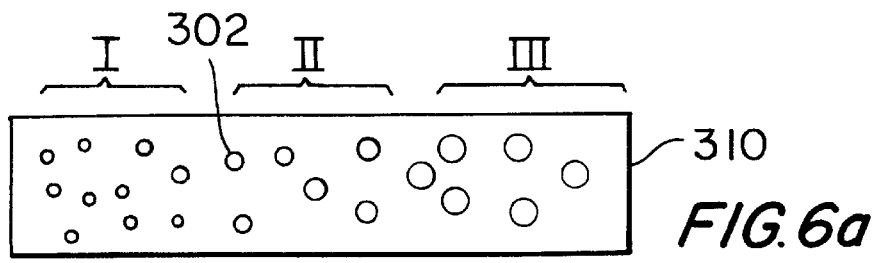
FIG. 6a is a side view of an illustrative graft structure in accordance with the present invention in which compliance is controlled by varying the pore size of the graft structure.
Figure 6B:
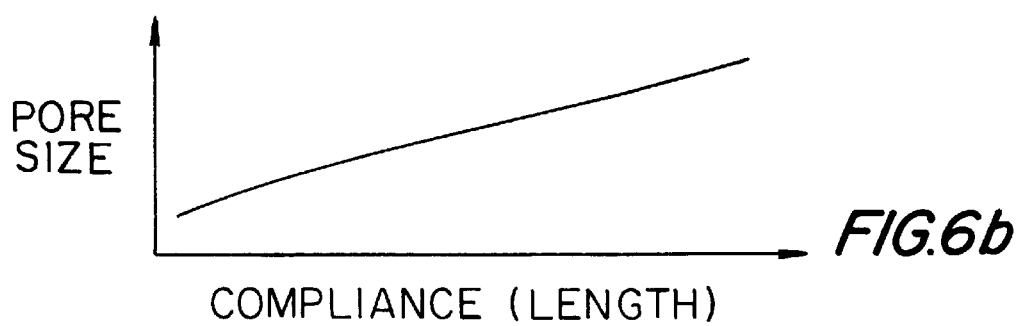

As shown in FIG. 6a, graft 310 may be provided with larger pores 302 in region II than in region I and larger pores in region III than in region II. This creates a compliance profile such as shown in FIG. 6b.

Figure 7A:
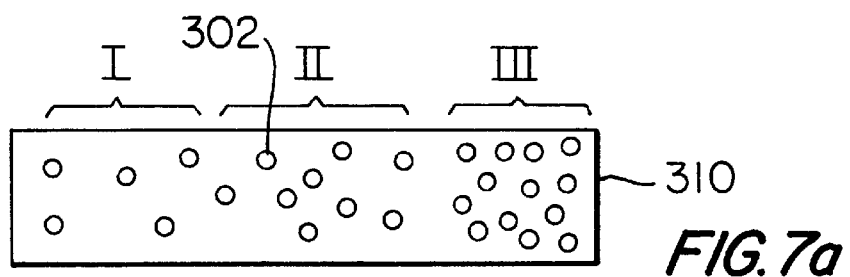
FIG. 7a is a side view of an illustrative graft structure in accordance with the present invention in which compliance is controlled by varying the quantity of pores in the graft structure.
Figure 7B:
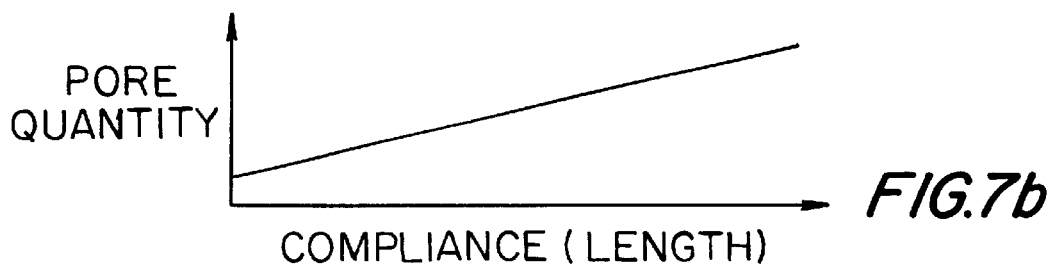

As shown in FIG. 7a, graft 310 may be provided with more pores 302 in region II than in region I and more pores 302 in region III than in region II. This creates a compliance profile such as shown in FIG. 7b. The distribution of pore quantities and pore sizes may be continuous or step-like. Both the pore size and pore quantity can be varied if desired.

Porous graft structures such as grafts 310 of FIGS. 6 and 7 may be formed using a coating made of an elastic material that is mixed with particles of a material that can be removed (e.g., by vaporization) after the coating has been applied to a frame (e.g., by spraying).

A number of different connector structures may be used to install grafts such as graft 10 (FIG. 1). For example, connector structures 116 of FIG. 8, which are formed from elastic rings with barbs 118, may be used to connect graft 210 to body organ tubing such as body organ tubing 16 and 18 of FIG. 1. Ring structures may be formed of any suitable material, such as an elastic polymer. Installation may be intraluminally (e.g., by radially compressing and delivering the grafts through the existing vascular system of the patient) or may use general surgical techniques. During installation of graft 210, connector structures 116 may be radially compressed, so that the ends of graft 210 may be inserted inside the corresponding ends of the body organ tubing to which graft 210 is to be attached. Once the ends of graft 210 have been positioned properly for graft attachment, connector structures 116 are released, which causes barbs 118 to penetrate the surrounding body organ tubing and thereby hold graft 210 in place.

Other suitable connector structures include serpentine wire structures, structures without barbs or hook, etc. Compliant connector structures that may be used include the connector structures described in Berg et al. U.S. patent application Ser. No. 08/946,742, filed Oct. 9, 1997, and Bachinski U.S. patent application Ser. No. 08/948,162, filed Oct. 9, 1997.

The compliances of the connector structures such as 116 that are used to install graft 10 (FIG. 1) are preferably matched to the compliances of the graft ends and the compliances of the body organ tubing to which the graft is attached. The compliances of connector structures 116 can be varied by controlling material parameters such as the durometer and Young's modulus of structures 116 (if the structures are elastomeric) or by varying the wire density, etc. (if the structures are formed from wire). Because the connector structures are relatively short along the longitudinal dimension of the graft, using such a connector structure will not greatly affect the overall compliance profile of the graft. Accordingly, although flexible structures with matched compliances are preferred, satisfactory results may be obtained using relatively inflexible connector structures if desired.

In order to match the compliance of a given graft to the body organ tubing that is to be repaired, the physician making the repair may asses the size of the body organ tubing being replaced, the particular locations in the body to which the graft ends are to be connected, and the graft length. Grafts with various compliance profiles are preferably made available to the physician, so that the physician may select a graft that matches the needs of the patient (e.g., age, degree of disease, type of disease, etc.).

If desired, tubular grafts with compliance gradients may be formed that have T-shapes or Y-shapes. All such grafts are herein collectively referred to as "tubular graft structures."

It will be understood that the foregoing is only illustrative of the principles of the invention, and that various modifications can be made by those skilled in the art without departing from the scope and spirit of the invention.

The invention claimed is:

1. A graft for installation in the body of a patient between portions of body organ tubing with different compliances, comprising a distensible artificial tubular graft structure with a substantially smooth compliance gradient along the length of the artificial tubular graft structure, wherein the distensible artificial tubular graft structure comprises a tubular elastic structure having pores, wherein the compliance of the distensible artificial tubular graft structure is determined at least in part by the quantity of the pores in the tubular elastic structure.

2. A graft for installation in the body of a patient between portions of body organ tubing with different compliances, comprising a distensible artificial tubular graft structure with a substantially smooth compliance gradient along the length of the artificial tubular graft structure, wherein the distensible artificial tubular graft structure comprises a tubular elastic structure having pores, wherein the compliance of the distensible artificial tubular graft structure is determined at least in part by the size and the quantity of the pores in the tubular elastic structure.

* * * * *